(12) United States Patent
Quint

(10) Patent No.: US 11,464,950 B2
(45) Date of Patent: Oct. 11, 2022

(54) BALLOON CATHETER AND METHOD OF PRODUCING SAME

(71) Applicant: BIOTRONIK AG, Buelach (CH)

(72) Inventor: Bodo Quint, Dettighofen (DE)

(73) Assignee: BIOTRONIK AG, Buelach (CH)

( * ) Notice: Subject to any disclaimer, the term of this patent is extended or adjusted under 35 U.S.C. 154(b) by 83 days.

(21) Appl. No.: 16/434,699

(22) Filed: Jun. 7, 2019

(65) Prior Publication Data
US 2019/0388658 A1 Dec. 26, 2019

(30) Foreign Application Priority Data
Jun. 25, 2018 (EP) .................................... 18179524

(51) Int. Cl.
*A61M 25/10* (2013.01)
*A61M 25/00* (2006.01)

(52) U.S. Cl.
CPC ...... *A61M 25/104* (2013.01); *A61M 25/1002* (2013.01); *A61M 25/1036* (2013.01); *A61M 25/0054* (2013.01); *A61M 2025/1088* (2013.01)

(58) Field of Classification Search
CPC ............ A61M 25/104; A61M 25/1002; A61M 25/0054; A61M 25/01; A61M 25/0015; A61M 25/0009; A61M 2025/1088; A61M 2025/1015; A61M 25/1011; A61M 25/1006

See application file for complete search history.

(56) References Cited

U.S. PATENT DOCUMENTS

| | | | | |
|---|---|---|---|---|
| 5,490,837 A | * | 2/1996 | Blaeser | A61M 25/104 604/103.11 |
| 5,545,134 A | * | 8/1996 | Hilaire | A61M 25/104 604/103.04 |
| 2007/0021771 A1 | * | 1/2007 | Oepen | A61M 25/0029 606/194 |
| 2010/0217234 A1 | * | 8/2010 | Grovender | A61M 25/0102 604/523 |

FOREIGN PATENT DOCUMENTS

| | | |
|---|---|---|
| EP | 1199082 A1 | 4/2002 |
| EP | 1787673 A1 | 5/2007 |
| EP | 2974765 A1 | 1/2016 |
| WO | 200145788 A1 | 6/2001 |

OTHER PUBLICATIONS

Berndorfer, Urs, EP Search Report for Application No. 18179524.6, dated Dec. 13, 2018.

* cited by examiner

*Primary Examiner* — James D Ponton
*Assistant Examiner* — Neeraja Gollamudi
(74) *Attorney, Agent, or Firm* — Greer, Burns & Crain, Ltd.; Steven P. Fallon

(57) ABSTRACT

A balloon catheter has an outer shaft which surrounds a shaft lumen. The outer shaft has a proximal outer shaft portion connected to a distal outer shaft portion. An inner shaft is in a distal portion of the shaft lumen. A guide wire lumen is in the inner shaft. An opening at a proximal end portion of the inner shaft permits the guide wire to be guided out from the outer shaft. A metallic tube is in the shaft lumen. The proximal end portion of the inner shaft is engaged with the metallic tube. A separate, elongate and metallic stiffening element is in the shaft lumen, and is connected to the metallic tube and protrudes from the metallic tube into the distal portion of the shaft lumen and into the proximal (Continued)

portion of the shaft lumen to stiffen portions of the outer shaft.

15 Claims, 4 Drawing Sheets

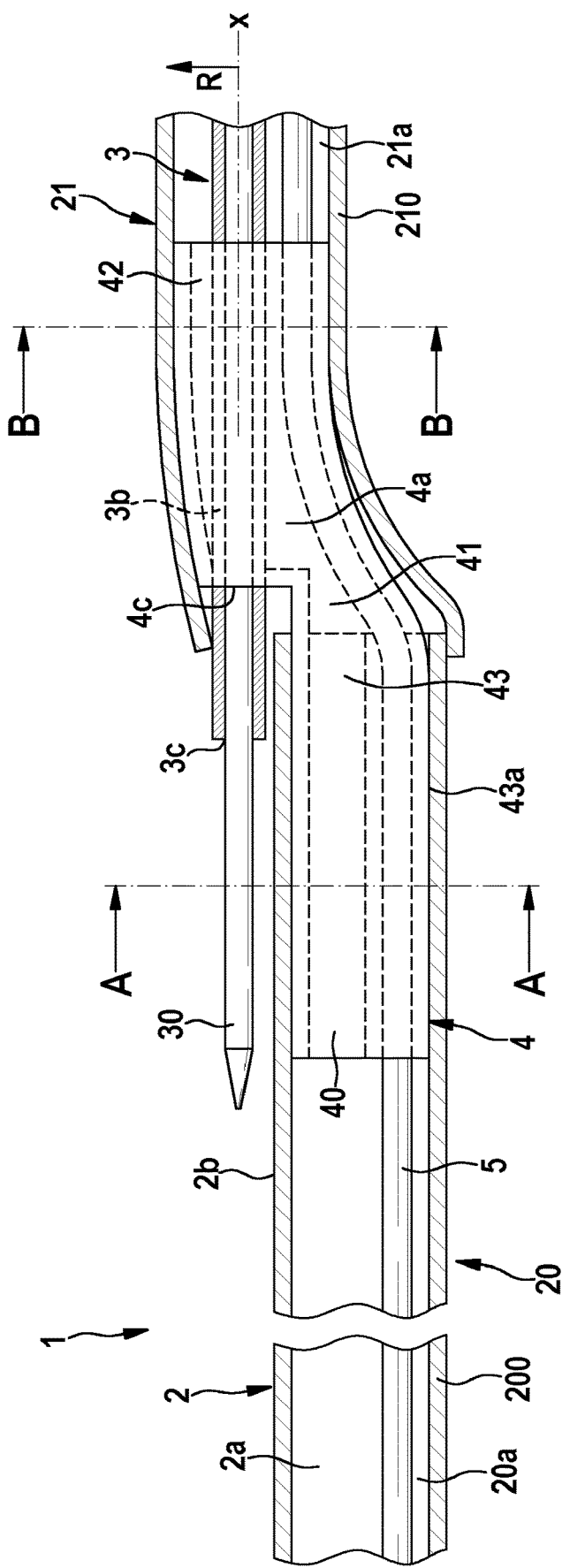
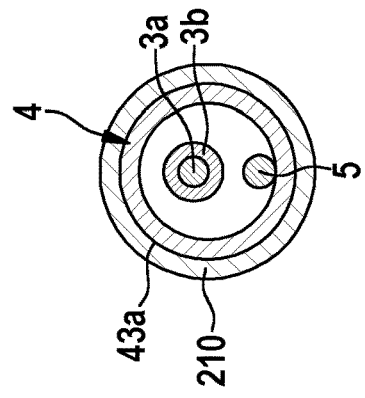
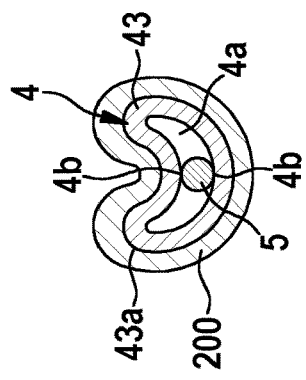

BALLOON CATHETER AND METHOD OF PRODUCING SAME

PRIORITY CLAIM

This application claims priority under 35 U.S.C. § 119 and all applicable statutes and treaties from prior European Application EP 18179524.6, filed Jun. 25, 2018.

FIELD OF THE INVENTION

The present invention relates to a balloon catheter, and to a method for producing a balloon catheter. One application of the invention is to percutaneous transluminal coronary angioplasty (PCTA) catheters. Another application of the invention is to balloon catheters used to unfold stents or heart valve prostheses.

BACKGROUND

A balloon catheter is a tubular structure, which for example can be introduced for therapeutic purposes into a body lumen, in particular a vessel, of a patient. A specific field of application is percutaneous transluminal coronary angioplasty (PCTA) catheters, which are used to widen or reopen a constricted or closed coronary vessel. The catheter has a balloon that can be inflated by a fluid (in particular compressed air) and expands in the vascular constriction. A catheter of this kind can be guided or pushed to the location of the vascular constriction with the aid of a guide wire.

Typical conventional balloon catheters have a two-membered shaft construction. A proximal shaft segment is provided, which is usually formed by a metallic tubular element (for example a hypotube) and is equipped at a joint with a coaxial portion. The proximal shaft segment is connected via the joint to a distal shaft segment, which in turn connected to the balloon. A guide wire exit point or opening is typically provided at the joint.

Three-membered shaft designs are also known. In such designs, the proximal shaft segment (for example hypotube) firstly transitions into a support tube and then transitions via a connection point, at which the guide wire exit point or the sideport is provided, into a distal and coaxial shaft segment.

For example, Jowett & Kelly document EP1084728A1, entitled A Balloon Catheter describes a catheter in which a relatively rigid and chamfered hypotube is connected via a transition region to a relatively soft distal module.

Furthermore, Garakani document US2010/0168669A1, entitled Balloon Catheter describes a catheter in which a relatively rigid proximal shaft portion and a distal shaft portion are connected to one another via a flexible transition element, wherein the distal shaft portion has a guide wire lumen.

SUMMARY OF THE INVENTION

A preferred balloon catheter has an outer shaft which surrounds a shaft lumen. The outer shaft has a proximal outer shaft portion connected to a distal outer shaft portion. An inner shaft is in a distal portion of the shaft lumen. A guide wire lumen is in the inner shaft. An opening at a proximal end portion of the inner shaft permits the guide wire to be guided out from the outer shaft. A metallic tube is in the shaft lumen. The proximal end portion of the inner shaft is engaged with the metallic tube. A separate, elongate and metallic stiffening element is in the shaft lumen, and is connected to the metallic tube and protrudes from the metallic tube into the distal portion of the shaft lumen and into the proximal portion of the shaft lumen to stiffen portions of the outer shaft.

BRIEF DESCRIPTION OF THE DRAWINGS

Further features and embodiments of the present invention will be described hereinafter in conjunction with the drawings, in which:

FIGS. 3A-3C shows a schematic sectional depiction of a further embodiment of a metallic tube of a catheter according to the invention.

DETAILED DESCRIPTION OF THE PREFERRED EMBODIMENTS

Figure 1:
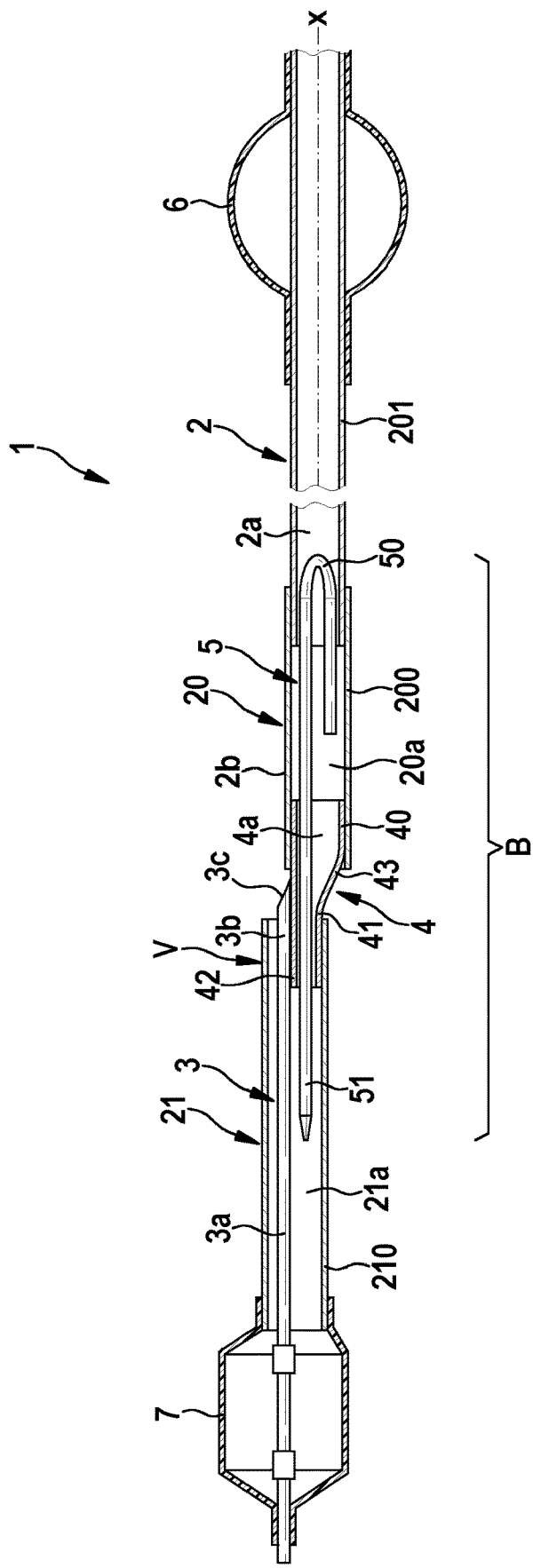
FIG. 1 shows a schematic sectional depiction of an embodiment of a metallic tube of a catheter according to the invention.

In accordance with the invention, in the lumen of the outer shaft there is arranged a metallic tube, via which the distal portion of the shaft lumen communicates with a proximal portion of the shaft lumen surrounded by the proximal outer shaft portion, wherein the proximal end portion of the inner shaft is engaged with the metallic tube, and wherein there is arranged in the shaft lumen a separate, elongate and metallic stiffening element, which is connected to the metallic tube and protrudes from the metallic tube into the distal portion of the lumen and into the proximal portion of the lumen in order to stiffen the outer shaft in some sections.

In accordance with an embodiment of the catheter according to the invention it is provided that the proximal outer shaft portion is connected to the distal outer shaft portion via a bonded connection, in particular a welded connection, wherein the connection extends in a circumferential direction of the metallic tube along an outer side of a wall of the metallic tube. The two outer shaft portions in accordance with an embodiment are furthermore also connected to the outer side of the wall of the metallic tube, in particular by a bonded, form-fit and/or force-fit connection.

In accordance with an embodiment of the catheter according to the invention it is provided that the inner shaft extends coaxially in the lumen of the distal outer shaft portion, at least in some sections.

A balloon catheter of the invention provides a catheter that has a guide wire opening which is relatively easy to produce for guiding a guide wire out from the catheter, such that at the same time a low sensitivity to bending is provided in the region of the guide wire opening.

The stiffening element in accordance with an embodiment is preferably a wire made of a metal. For example, the metal may be stainless steel, such as AISI 304/302/316, or may be formed by nickel alloys, such as Inconel or Nimonic 90. Titanium, aluminium, copper or alloys thereof are further potential materials. In particular, copper alloys such as $CuBe_2$ are advantageous due to their elasticity and insensitivity to corrosion, since a stiffening element made of a material of this kind is less susceptible to connection defects during a subsequent crimping of a stent onto a balloon.

The metallic tube in accordance with an embodiment furthermore likewise consists of a metal, in particular of a stainless steel such as AISI 304/302/316.

It is furthermore provided in accordance with an embodiment of the catheter according to the invention that the metallic tube has a proximal end portion, a distal end portion and in particular a wall extending in the circumferential direction of the metallic tube, which wall surrounds a lumen of the metallic tube.

It is furthermore provided in accordance with an embodiment of the catheter according to the invention that the metallic tube is curved or shaped in such a way that the distal end portion of the metallic tube extends offset in relation to the proximal end portion of the metallic tube. This curvature is preferably produced by a reshaping of the metallic tube.

It is furthermore provided in accordance with an embodiment of the catheter according to the invention that the stiffening element extends through the lumen of the metallic tube and is securely clamped in the lumen of the metallic tube, in particular by reshaping of the metallic tube, and/or is connected to the metallic tube via a welded connection.

It is furthermore provided in accordance with an embodiment of the catheter according to the invention that the opening of the proximal end portion of the inner shaft is arranged on an outer side of the outer shaft laterally of the metallic tube, wherein in particular the opening is formed on an end side of the proximal end portion, i.e. on a proximal end of the inner shaft. An opening of this kind is therefore also referred to as a sideport.

It is furthermore provided in accordance with an embodiment of the catheter according to the invention that the distal end portion of the metallic tube has a concave hollow on an outer side of the wall, in which concave hollow at least part of the proximal end portion of the inner shaft engages or is arranged, whereby the above-mentioned engagement is produced.

It is furthermore provided in accordance with an embodiment of the catheter according to the invention that the hollow is formed in the wall by reshaping the wall of the metallic tube.

It is furthermore provided in accordance with an embodiment of the catheter according to the invention that the stiffening element is clamped in the lumen of the metallic tube by the hollow.

It is furthermore provided in accordance with an embodiment of the catheter according to the invention that the proximal end portion of the inner shaft is engaged with the metallic tube in that the proximal end portion of the inner shaft protrudes into the distal end portion of the metallic tube and extends in the lumen of the metallic tube through the distal end portion of the metallic tube.

It is furthermore provided in accordance with an embodiment of the catheter according to the invention that the wall of the metallic tube has a through-opening in a connection portion or in a middle portion of the metallic tube, which connects the proximal end portion of the metallic tube to the distal end portion of the metallic tube, through which through-opening part of the proximal end portion of the inner shaft is guided out from the lumen of the metallic tube.

It is furthermore provided in accordance with an embodiment of the catheter according to the invention that the through-opening (with linearly arranged outer shaft) extends in a direction running normal to a longitudinal axis of the outer shaft, such that the inner shaft in the region of the through-opening extends parallel to the longitudinal axis and the guide wire can be guided out from the guide wire lumen or the outer and inner shaft via the opening of the inner shaft linearly, i.e. without significant curvature.

It is furthermore provided in accordance with an embodiment of the catheter according to the invention that the stiffening element is securely clamped in the lumen of the metallic tube in the proximal end portion of the tube lumen. In this regard it can be provided that the stiffening element is securely clamped in the lumen of the metallic tube in particular by reshaping, in particular by flattening or denting the proximal end portion of the metallic tube.

It is furthermore provided in accordance with an embodiment of the catheter according to the invention that the proximal outer shaft portion has a metallic tube structure (hypotube), which is connected to the metallic tube or to the distal outer shaft portion via a flexible hose element of the proximal outer shaft portion, wherein in particular the stiffening element extends with a proximal end portion (starting from the metallic tube) into a portion of the lumen of the outer shaft surrounded by the metallic tube structure.

It is furthermore provided in accordance with an embodiment of the invention that the flexible metallic tube of the proximal outer shaft portion has a wall that is formed by one or more of the following materials or includes one or more of the following materials: a polymer, polyamide, polyurethane, polyester such as polyethylene terephthalate, polyester copolymers such as Hyrtel (tradename), or polyester block amide such as PEBAX (tradename). The aforementioned materials are preferred since they can be used to produce a welded or fused connection to a broad range of materials.

It is furthermore provided in accordance with an embodiment of the catheter according to the invention that the distal outer shaft portion has a hose element that is connected to the metallic tube or to the proximal outer shaft portion, wherein in particular the stiffening element extends with a distal end portion (starting from the metallic tube) into a portion of the lumen of the outer shaft surrounded by the hose element of the distal outer shaft portion.

It is furthermore provided in accordance with an embodiment of the invention that the flexible hose element of the distal outer shaft portion has a wall that is formed by one or more of the following materials or includes one or more of the following materials: a polymer, polyamide, polyurethane, polyester such as polyethylene terephthalate, polyester copolymers such as Hyrtel (tradename), or polyester block amide such as PEBAX (tradename). The aforementioned materials are preferred since they can be used to produce a welded or fused connection to a broad range of plastics materials having different mechanical properties.

It is provided in accordance with a further embodiment of the invention that the distal outer shaft portion, in particular the hose element of the distal outer shaft portion, is connected at a distal end of the distal outer shaft portion to an unfoldable, in particular inflatable balloon.

A further aspect of the present invention relates to a method for producing the catheter (in particular balloon catheter).

In this regard a method is disclosed for producing a catheter (in particular a catheter according to the invention), wherein a proximal outer shaft portion and a distal outer shaft portion of the catheter or outer shaft to be produced are provided, wherein an inner shaft is arranged in a portion of a lumen of the catheter to be produced surrounded by the distal shaft portion and has a guide wire lumen for receiving a guide wire, and wherein a metallic tube is provided, wherein an elongate and metallic stiffening element is secured in a lumen of the metallic tube by reshaping the metallic tube and/or by forming a welded connection at the metallic tube, wherein a proximal end portion of the inner shaft is brought into engagement with the metallic tube, and wherein the proximal outer shaft portion and the distal outer shaft portion are connected to the metallic tube such that the stiffening element is guided from the metallic tube into a proximal portion of the lumen of the outer shaft surrounded by the proximal outer shaft portion and into the distal portion of the lumen of the outer shaft.

The mentioned reshaping is performed in accordance with an embodiment of the method according to the invention by a die and by a press.

In accordance with an embodiment of the method according to the invention it is provided that the metallic tube is curved prior to the connection to the distal and the proximal outer shaft portion, preferably by a reshaping of the metallic tube, preferably by the die and by the press, in such a way that the distal end portion of the metallic tube extends offset in relation to the proximal end portion of the metallic tube.

It is furthermore provided in accordance with an embodiment of the method according to the invention that an opening of the proximal end portion of the inner shaft via which a guide wire can be guided out from the guide wire lumen or the catheter is arranged laterally of the metallic tube, wherein in particular the opening is formed on an end face of the proximal end portion, i.e. on a proximal end of the inner shaft (see also above).

It is furthermore provided in accordance with an embodiment of the method according to the invention that a distal end portion of the metallic tube is reshaped, preferably by the die and by the press, such that the distal end portion of the metallic tube is provided with a concave hollow on an outer side of a wall of the metallic tube, wherein in particular the aforementioned engagement between inner shaft and metallic tube is produced by arranging at least part of the proximal end portion of the inner shaft in the hollow.

It is furthermore provided in accordance with an embodiment of the method that the stiffening element is clamped in the lumen of the metallic tube by the hollow (see also above).

It is furthermore provided in accordance with an alternative embodiment of the method according to the invention that the proximal end portion of the inner shaft is brought into engagement with the metallic tube by introducing the proximal end portion of the inner shaft into the distal end portion of the metallic tube, such that it extends in the lumen of the metallic tube through the distal end portion of the metallic tube.

It is furthermore provided in this regard in accordance with an embodiment of the method according to the invention that a through-opening is formed in the wall of the metallic tube in a connection portion or in a middle portion of the metallic tube connecting a proximal end portion of the metallic tube to the distal end portion of the metallic tube, through which through-opening part of the proximal end portion of the inner shaft is guided out from the lumen of the metallic tube.

It is furthermore provided in accordance with an embodiment of the method according to the invention that the stiffening element is securely clamped in the lumen of the metallic tube in the proximal end portion of the metallic tube, in particular by reshaping, in particular by flattening or denting the proximal end portion of the metallic tube.

FIG. 1 shows a schematic sectional view of a catheter according to the invention 1, with an elongate outer shaft 2, wherein the outer shaft 2 surrounds a shaft lumen 2a of the catheter 1 and also has a proximal outer shaft portion 20 and a distal outer shaft portion 21 connected to the proximal outer shaft portion 20. The two outer shaft portions 20, 21 surround, respectively, a portion 20a and 21a of the shaft lumen 2a, wherein the two portions 20a, 21a of the shaft lumen 2a communicate with one another, i.e. are fluidically connected to one another. Furthermore, an inner shaft 3 is arranged in the distal portion 21a of the shaft lumen 2a and has a guide wire lumen 3a for receiving a guide wire 30, wherein the inner shaft 3, at a proximal end portion 3b of the inner shaft 3, has an opening 3c, via which the guide wire 30 can be guided out from the outer shaft 2. The inner shaft 3 in accordance with an embodiment extends coaxially at least in some sections in the distal portion 21a of the shaft lumen 2a.

The catheter 1 is embodied in the present case is a balloon catheter and accordingly has a balloon 7 connected to the distal outer shaft portion 21, which balloon for example can be inflated by compressed air, which can be introduced into the balloon 7 via the portions 20a and 21a of the shaft lumen 2a. The inner shaft 3 extends through the balloon 7, such that the balloon 7 can be guided in a vessel of a patient by the guide wire 30 to a site of use.

In accordance with the invention the catheter 1 has a metallic tube 4, which is arranged in the shaft lumen 2a of the outer shaft 2, such that the distal portion 21a and the proximal portion 20a of the shaft lumen 2a communicate via a lumen 4a of the metallic tube 4 surrounded by a wall 43 of the metallic tube 4. In other words, in order to inflate the balloon 7, the compressed air or another suitable flow can be introduced into the proximal portion 20a of the shaft lumen 2a, flows through the lumen 4a of the metallic tube 4, and passes via the portion 21a of the shaft lumen 2a adjoined thereto into the balloon 7.

The distal and proximal outer shaft portion 21, 20 are furthermore connected to one another in the region of an outer side 43a of the metallic tube 4, in particular in a bonded manner, for example by welding the two portions 20, 21 to one another. Furthermore, the two portions 20, 21 of the outer shaft 2 are connected in a bonded and/or form-fitting and/or force-fitting manner to the outer side 43a of the wall 43 of the metallic tube 4.

The catheter 1 furthermore has a stiffening element 5 in order to stiffen the outer shaft 2 in some sections in the region of the lateral opening 3c of the inner shaft (denoted in FIG. 1 as transition region B), which stiffening element is provided in particular in the form of a separate metal wire, which is secured to the metallic tube 4, in particular by securely clamping the stiffening element 5 in the metallic tube 4 and/or by a bonded connection (for example welded connection). The stiffening element 5 is in particular arranged in the lumen 4a of the metallic tube 4 in such a way that it protrudes into the distal portion 21a of the shaft lumen 2a and into the proximal portion 20a of the shaft lumen 2a in order to stiffen the transition region B.

The opening 3c preferably forms what is known as a sideport and is arranged laterally on the catheter 1 accordingly, i.e. on an outer side 2b of the outer shaft 2. Here, the opening 3c is preferably provided at a transition between the two outer shaft portions 20, 21, which lies against the outer side 43a of the metallic tube 4.

The proximal end portion 3b of the inner shaft 3 is preferably enclosed in a sealed manner in the outer shaft 2 when the two outer shaft portions 20, 21 are connected.

As indicated in FIG. 1, the metallic tube 4 has a proximal end portion 40 and a distal end portion 42, which in particular are connected to one another via a connection portion 41. Here, the metallic tube 4, in particular the connection or middle portion 41, can be curved in such a way that the distal end portion 42 of the metallic tube 4—in relation to the longitudinal axis x of the outer shaft 2—extends offset relative to the proximal end portion 40 of the metallic tube 4.

Furthermore, the proximal outer shaft portion 20 preferably has a metallic tube structure 201, which is also referred to as a hypotube and which is connected via a flexible hose element 200 of the proximal outer shaft portion 20 to the metallic tube 4 or a flexible hose element 210 of the distal outer shaft portion 42 (via the above-described, for example bonded connection). This metallic tube structure 201 is furthermore secured in particular to a grip 6 for handling the catheter 1. With regard to the tube structure 201, it is also provided that the stiffening element 5 extends with a proximal end portion 50 into a portion of the shaft lumen 2a, which is surrounded by the metallic tube structure 201.

Furthermore, it is likewise preferably provided that the stiffening element 5 extends with a distal end portion 51 into a portion of the shaft lumen 2a that is surrounded by the hose element 210 of the distal outer shaft portion 21.

A sufficient stiffening of the outer shaft 2 is hereby produced in the region of the lateral opening 3c.

Figure 2B:
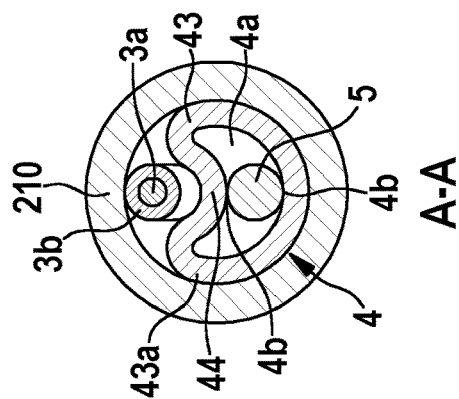
FIGS. 2A-2B show a schematic sectional depiction of an embodiment of a metallic tube of a catheter according to the invention.
Figure 2A:
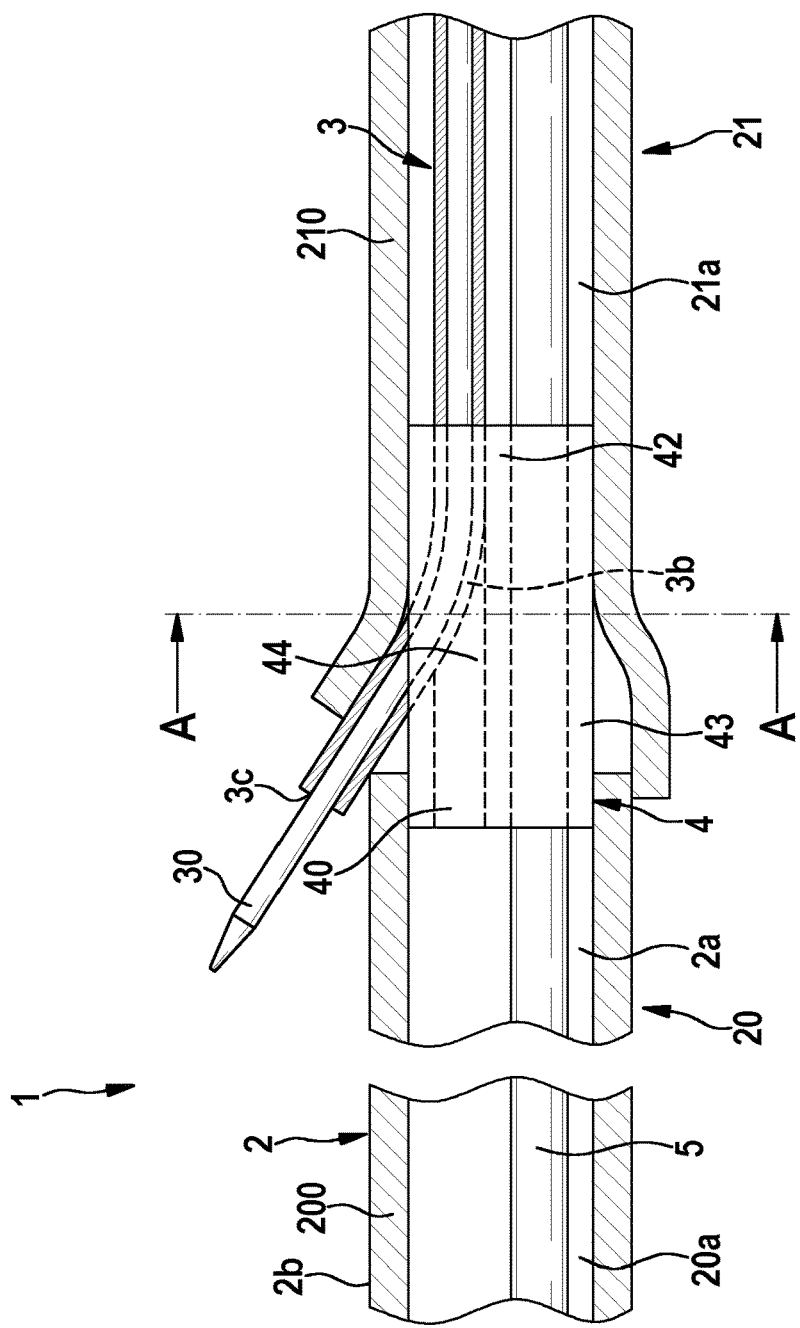

FIGS. 2 and 3 show in detail two different embodiments in respect of the more detailed design of the metallic tube 4.

Figure 4B:
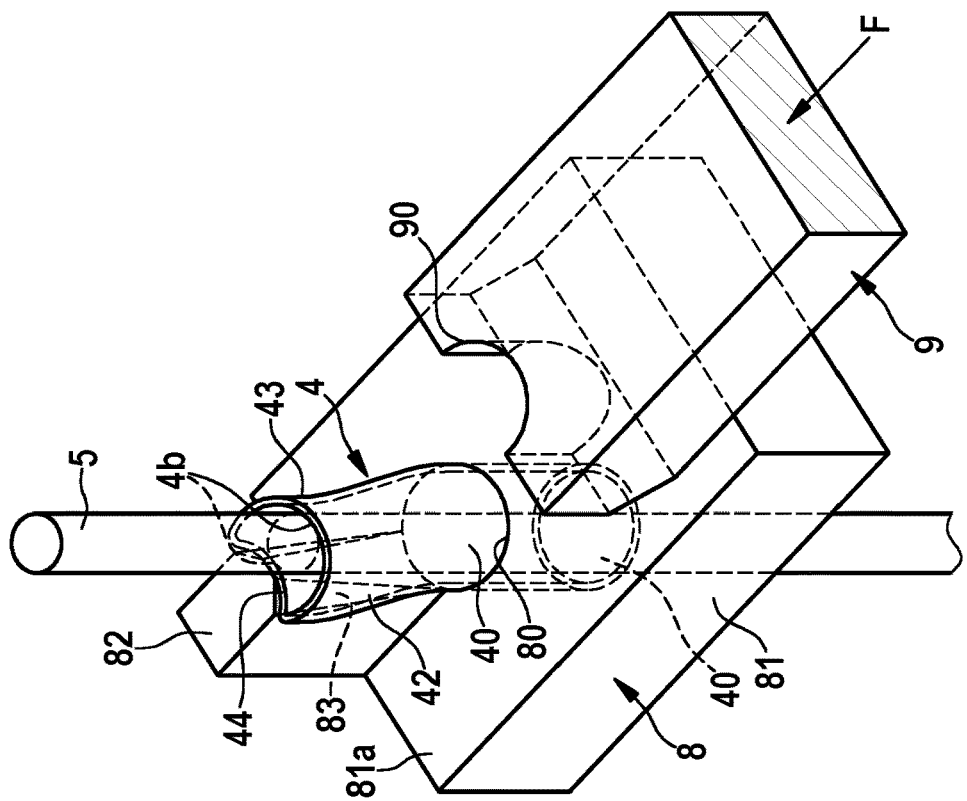
FIGS. 4A-4B shows a perspective view of a die and a press for reshaping the metallic tube in the production of a catheter according to the invention, without metallic tube (A) and with metallic tube (B).

In accordance with the variant shown in FIG. 2 it is provided that the distal end portion 42 of the metallic tube 4 has, on an outer side 43a of the wall 43, a concave hollow 44, in which at least part of the proximal end portion 3b of the inner shaft 3 engages or is arranged. The hollow 44 is preferably formed in the wall 43 by reshaping the wall 43 of the metallic tube 4. Reshaping can be performed for example with the aid of the tool shown in FIG. 4, which has a die 8 and a press 9 to reshape the metallic tube 4.

As a result of the reshaping, the stiffening element 5 is also clamped by the hollow 44 in the distal end portion 42 in the lumen 4a of the metallic tube 4 in that two mutually opposed regions 4b of the inner side of the metallic tube 4 press against the stiffening element 5 as a result of the shaping of the hollow 44. FIG. 1 shows the location of this connection along the longitudinal axis x as connection point V.

It is furthermore preferably provided that the proximal and the distal outer shaft portion 20, 21 are overlapped and welded to one another in the shown cross-sectional plane A of FIG. 2, wherein the proximal end portion 3b of the inner shaft 3 is enclosed in a sealed manner between the two portions 20, 21 of the outer shaft 2.

According to FIG. 2, the metallic tube 4, apart from the hollow 44, is substantially cylindrical, but may also have the curvature (see above) shown in FIG. 1.

FIG. 3 shows an alternative embodiment of the metallic tube 4. Here, in particular the connection portion 41 of the metallic tube 4 is reshaped or curved in such a way that the proximal end portion 40 and a distal end portion 42 extend offset in relation to one another. Furthermore, a through-opening 4c is formed in the wall 43 in the connection portion 41 and extends along a direction R oriented perpendicularly to the longitudinal axis x. This also includes the possibility that the opening plane of the through-opening 4c extends at an incline to the longitudinal axis x.

According to FIG. 3 it is provided that the proximal end portion 3b of the inner shaft 3 is engaged with the metallic tube 4 in that the proximal end portion 3b of the inner shaft 3 protrudes into the distal end portion 42 of the metallic tube 4 and in the lumen 4 of the metallic tube 4 extends through the distal end portion 42 of the metallic tube 4 and, in part, is guided out from the metallic tube 4 and in particular the outer shaft 2 through the through-opening 4c.

On account of the arrangement of the through-opening 4c or the curvature of the metallic tube 4, it is possible that the inner shaft 3, in the region of the through-opening 4c, can extend parallel to the longitudinal axis x of the outer shaft 2, and the guide wire 30 correspondingly can be guided out from the guide wire lumen 3a or the outer and inner shaft 2, 3 linearly, i.e. without significant curvature, via the opening 3c of the inner shaft 3.

In contrast to the variant shown in FIG. 2, it is provided that the stiffening element 5 is securely clamped in the lumen 4a of the metallic tube 4 in the proximal end portion 40 of the metallic tube 4. FIG. 2 in this regard shows a section along the plane A. The proximal end portion 40 of the metallic tube 4 is then reshaped, for example by denting or flattening of the wall 43, in order to securely clamp the stiffening element 5, so that two mutually opposed regions 4b of the inner side of the wall 43 of the metallic tube again press against the stiffening element 5.

Alternatively or additionally, the stiffening element 5 in all embodiments can also be connected to the metallic tube 4 via a welded connection.

The hollow 44 described in conjunction with FIGS. 1 and 2 can be shaped in particular by the tool shown in FIG. 4. The tool has a die 8 and associated press 9.

Figure 4A:
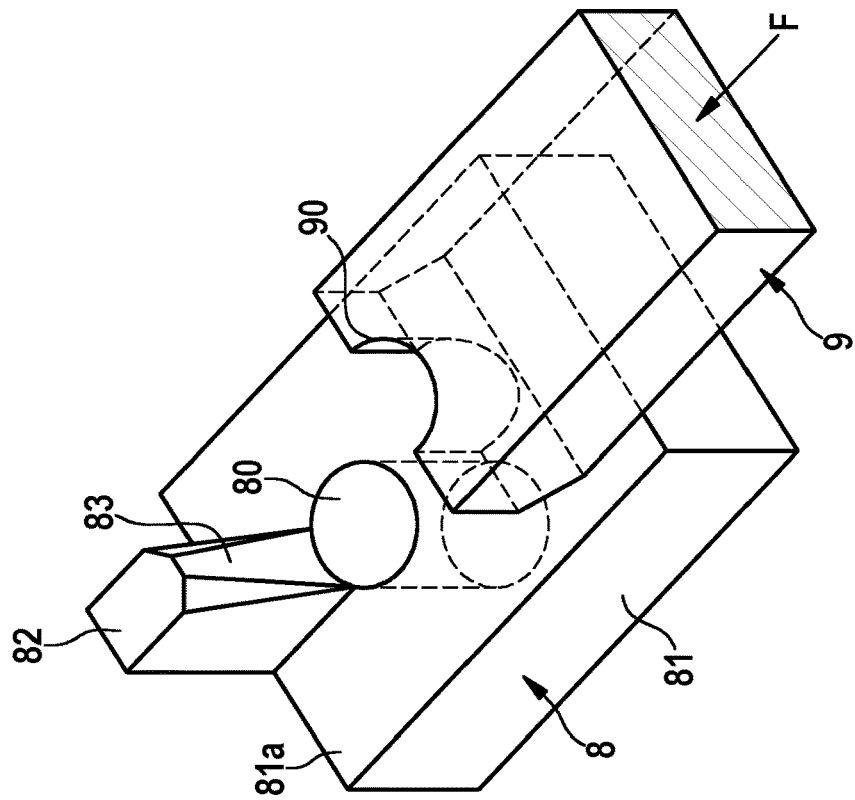

According to FIG. 4(A) the die 8 has a cylindrical through-opening 80, which is formed in a base 81 of the die 8, wherein a protrusion 82 protrudes from the base 81 from an edge of the opening 80. The protrusion has an outer side 83, which forms a positive mould for the hollow 44 to be formed. In order to form the hollow 44 and in particular in order to form a curvature of the connection portion 41 of the metallic tube 4, a cylindrical blank 4 is introduced into the through-opening 80 in accordance with FIG. 4(B), such that the later proximal end portion of the metallic tube is arranged in the through-opening 80. Furthermore, the stiffening element 5 is inserted into the lumen 4a of the blank 4 or metallic tube 4. The press 9 is then moved along a surface 81a of the base in the direction of the protrusion 82, wherein an end face 90 of the press 9 comes into engagement with the blank 4 and presses this with a defined force F against the outer side 83 of the protrusion 82. Here, the wall 3 of the blank 4 in the region of the distal end portion 4 of the blank 4 lies around the outer side 83 or the protrusion 82, thus forming the hollow 44 and in particular the aforementioned curvature of the metallic tube 4. At the same time, the distal end portion 42 of the metallic tube 4 protruding out from the through-opening 80 is clamped in the lumen 4a of the metallic tube 4 on account of the shaping of the hollow 44 (see also above).

It will be apparent to those skilled in the art that numerous modifications and variations of the described examples and embodiments are possible in light of the above teaching. The disclosed examples and embodiments may include some or all of the features disclosed herein. Therefore, it is the intent to cover all such modifications and alternate embodiments as may come within the true scope of this invention.

What is claimed is:

1. A balloon catheter comprising an outer shaft which surrounds a shaft lumen, the outer shaft having a proximal outer shaft portion and a distal outer shaft portion, an inner shaft in a distal portion of the shaft lumen, a guide wire lumen in the inner shaft for receiving a guide wire, a side port on an outer side of the outer shaft at a proximal end portion of the inner shaft via which the guide wire can be guided out from the outer shaft, a metallic tube arranged laterally of the side port in the shaft lumen, via which the distal portion of the shaft lumen communicates with a proximal portion of the shaft lumen surrounded by the proximal outer shaft portion, wherein a part of the proximal end portion of the inner shaft is engaged with the metallic tube, further comprising a separate, elongate and metallic stiffening element in the shaft lumen, wherein the stiffening element extends through a lumen of the metallic tube, is securely clamped by a shaped portion of the metallic tube and protrudes from the metallic tube into the distal portion of the shaft lumen and into the proximal portion of the shaft lumen to stiffen portions of the outer shaft.

2. The catheter according to claim 1, wherein the metallic tube has a proximal end portion, a distal end portion and a wall, which surrounds the lumen of the metallic tube.

3. The catheter according claim 2, wherein the distal end portion of the metallic tube is shaped to define a concave hollow on an outer side of the wall, and at least part of the proximal end portion of the inner shaft engages the concave hollow.

4. The catheter according to claim 2, wherein the metallic tube is curved such that the distal end portion of the metallic tube extends offset relative to the proximal end portion of the metallic tube.

5. The catheter according to claim 2, wherein the proximal end portion of the inner shaft is engaged with the metallic tube such that the proximal end portion of the inner shaft protrudes into the distal end portion of the metallic tube and extends in the lumen of the metallic tube through the distal end portion of the metallic tube.

6. The catheter according to claim 2, wherein the wall of the metallic tube, in a connection portion of the metallic tube that connects the proximal end portion of the metallic tube to the distal end portion of the metallic tube, has a through-opening through which part of the proximal end portion of the inner shaft is guided out from the lumen of the metallic tube.

7. The catheter according to claim 6, wherein the through-opening extends along a direction running normal to a longitudinal axis of the outer shaft.

8. The catheter according to claim 2, wherein the shaped portion is in the proximal end portion of the metallic tube.

9. The catheter according to claim 1, wherein the distal outer shaft portion has a hose that is connected to the metallic tube and/or to a flexible hose element of the proximal outer shaft portion, and the stiffening element extends with a distal end portion into a portion of the shaft lumen surrounded by the flexible hose.

10. The catheter according to claim 1, wherein the distal outer shaft portion and the proximal outer shaft portion are furthermore connected to one another by a weld in a region of an outer side wall of the metallic tube.

11. The catheter according to claim 10, wherein the weld is a circumferential weld of proximal and distal shaft portions to outer side wall of metallic tube.

12. The catheter according to claim 1, the proximal and distal outer shaft portions being at least partially offset.

13. The catheter according to claim 1, comprising a welded connection between the stiffening element and the metallic tube.

14. A balloon catheter comprising an outer shaft which surrounds a shaft lumen, the outer shaft having a proximal outer shaft portion and a distal outer shaft portion, an inner shaft in a distal portion of the shaft lumen, a guide wire lumen in the inner shaft for receiving a guide wire, an opening at a proximal end portion of the inner shaft via which the guide wire can be guided out from the outer shaft, a metallic tube in the shaft lumen, via which the distal portion of the shaft lumen communicates with a proximal portion of the shaft lumen surrounded by the proximal outer shaft portion, wherein a part of the proximal end portion of the inner shaft is engaged with the metallic tube, further comprising a separate, elongate and metallic stiffening element in the shaft lumen, wherein the stiffening element is connected to the metallic tube and protrudes from the metallic tube into the distal portion of the shaft lumen and into the proximal portion of the shaft lumen to stiffen portions of the outer shaft, wherein the metallic tube has a proximal end portion, a distal end portion and a wall, which surrounds a lumen of the metallic tube, and wherein the distal end portion of the metallic tube has a concave hollow on an outer side of the wall and wherein the stiffening element is clamped in the lumen of the metallic tube by the concave hollow.

15. A balloon catheter comprising an outer shaft which surrounds a shaft lumen, the outer shaft having a proximal outer shaft portion and a distal outer shaft portion, an inner shaft in a distal portion of the shaft lumen, a guide wire lumen in the inner shaft for receiving a guide wire, an opening at a proximal end portion of the inner shaft via which the guide wire can be guided out from the outer shaft, a metallic tube in the shaft lumen, via which the distal portion of the shaft lumen communicates with a proximal portion of the shaft lumen surrounded by the proximal outer shaft portion, wherein a part of the proximal end portion of the inner shaft is engaged with the metallic tube, further comprising a separate, elongate and metallic stiffening element in the shaft lumen, wherein the stiffening element is connected to the metallic tube and protrudes from the metallic tube into the distal portion of the shaft lumen and into the proximal portion of the shaft lumen to stiffen portions of the outer shaft, wherein the proximal outer shaft portion has a second metallic tube, which is connected to the metallic tube and/or to a flexible hose of the distal outer shaft portion via a flexible hose element of the proximal outer shaft portion, and the stiffening element extends with a proximal end portion into a portion of the shaft lumen surrounded by the second metallic tube.

* * * * *